US009579341B2

(12) United States Patent
Doshi et al.

(10) Patent No.: US 9,579,341 B2
(45) Date of Patent: Feb. 28, 2017

(54) PRESERVED COMPOSITIONS CONTAINING HYALURONIC ACID OR A PHARMACEUTICALLY-ACCEPTABLE SALT THEREOF AND RELATED METHODS

(71) Applicant: JOHNSON & JOHNSON CONSUMER INC., Skillman, NJ (US)

(72) Inventors: Uday Doshi, Randolph, NJ (US); Kenneth T. Holeva, Phillipsburg, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 105 days.

(21) Appl. No.: 14/086,548

(22) Filed: Nov. 21, 2013

(65) Prior Publication Data

US 2015/0141368 A1 May 21, 2015

Related U.S. Application Data

(63) Continuation of application No. 11/803,873, filed on May 16, 2007, now Pat. No. 8,609,634.

(51) Int. Cl.
| | | |
|---|---|---|
| *C08B 37/08* | (2006.01) | |
| *A61K 31/728* | (2006.01) | |
| *A61K 9/00* | (2006.01) | |
| *A61K 47/18* | (2006.01) | |
| *A61K 47/36* | (2006.01) | |

(52) U.S. Cl.
CPC ........... *A61K 31/728* (2013.01); *A61K 9/0043* (2013.01); *A61K 9/0048* (2013.01); *A61K 47/18* (2013.01); *A61K 47/36* (2013.01); *C08B 37/0072* (2013.01)

(58) Field of Classification Search
None
See application file for complete search history.

(56) References Cited

U.S. PATENT DOCUMENTS

| | | | |
|---|---|---|---|
| 4,371,522 A | 2/1983 | Gilbard | |
| 4,443,432 A | 4/1984 | Garabedian et al. | |
| 4,711,249 A | 12/1987 | Brooks | |
| 5,342,620 A | 8/1994 | Chowhan | |
| 5,578,578 A | 11/1996 | Hecht et al. | |
| 5,770,628 A | 6/1998 | Cantoro | |
| 6,503,497 B2 | 1/2003 | Chowhan et al. | |
| 2005/0074504 A1 | 4/2005 | Chowhan et al. | |
| 2005/0147679 A1 | 7/2005 | Petito et al. | |
| 2005/0196370 A1* | 9/2005 | Yu | A61K 9/0048 424/70.13 |
| 2006/0069162 A1 | 3/2006 | Asada et al. | |
| 2008/0021101 A1* | 1/2008 | Jimenez-Bayardo et al. | 514/530 |
| 2008/0287672 A1 | 11/2008 | Doshi et al. | |
| 2010/0234319 A1* | 9/2010 | Yu | A61H 35/02 514/54 |

FOREIGN PATENT DOCUMENTS

| | | |
|---|---|---|
| EP | 0464727 | 8/1992 |
| EP | 0976407 | 2/2000 |
| EP | 1759702 | 3/2007 |
| JP | 1246227 | 10/1989 |
| JP | 296515 | 4/1990 |
| JP | 04-069342 | 4/1992 |
| JP | 08012571 A | 1/1996 |
| JP | 9176020 | 7/1997 |
| JP | 3050898 | 6/2000 |
| JP | 2002020279 | 1/2002 |
| JP | 2002356420 | 12/2002 |
| JP | 2004315472 | 11/2004 |
| WO | 9409795 | 5/1994 |
| WO | 2004004744 | 1/2004 |
| WO | 2005115401 | 12/2005 |

OTHER PUBLICATIONS

Hyaluronic Acid and Replacement of Vitreous and Aqueous Humor, EA Balazs, Mod. Prob. Of Opthalmology, vol. 10, pp. 3-21, 1972.

* cited by examiner

*Primary Examiner* — Eric Olson

(57) ABSTRACT

The invention provides a composition containing hyaluronic acid (HA) or a pharmaceutically-acceptable salt thereof preserved with a cationic preservative and related methods. In one embodiment, the pharmaceutically-acceptable salt is sodium hyaluronate. In another embodiment, the cationic preservative includes benzalkonium.

14 Claims, No Drawings

PRESERVED COMPOSITIONS CONTAINING HYALURONIC ACID OR A PHARMACEUTICALLY-ACCEPTABLE SALT THEREOF AND RELATED METHODS

CROSS-REFERENCE TO RELATED APPLICATION

The present application is a continuation of U.S. patent application Ser. No. 11/803,873, filed May 16, 2007, the entirety of which application is hereby incorporated herein by reference as if fully set forth herein.

TECHNICAL FIELD

The invention relates generally to preserved compositions containing hyaluronic acid (HA) or a physiologically-acceptable salt thereof, and more particularly, to HA compositions preserved with cationic preservatives such as benzalkonium chloride (BAK).

BACKGROUND OF THE INVENTION

Hyaluronic acid (HA) is a mucopolysaccharide found in various physiological fluids, including vitreous humor. The ability of HA to retain water has made it popular as a lubricant or wetting agent in various health care and pharmaceutical compositions, such as ophthalmic, otic, and nasal compositions.

To reduce the likelihood of infection due to microbial growth within compositions administered to an individual, such compositions typically include an antimicrobial preservative. One particularly effective antimicrobial preservative is benzalkonium chloride (BAK). However, it has been observed that HA and cationic preservatives, such as BAK, are incompatible, resulting in their conjugation and precipitation, thereby reducing both the lubricating and preservative properties of the composition. While the loss of such properties may sometimes be overcome by increasing the concentration of one or both compounds, BAK is believed to cause corneal disorders at high concentrations.

Similar precipitation has been noted between BAK and latanoprost. U.S. Patent Application Publication No. 20060069162 to Asada et al. discloses several methods for avoiding such precipitation. These include the addition of a surfactant, the use of a particular species of BAK (i.e., $[C_6H_5CH_2N(CH_3)R]Cl$, wherein R is alkyl having 12 carbon atoms ($BAK-C_{12}$)), and/or the addition of a nonionic tonicity agent. Such methods are unacceptable, however, as they require the inclusion of additional components to the composition, which increases complexity, expense, and the likelihood of adverse interactions, and/or the restriction of one component to a purified, and more expensive, species.

To this extent, a need exists for preserved compositions containing HA that do not suffer from the defects known in the art.

SUMMARY OF THE INVENTION

The invention provides a composition containing hyaluronic acid (HA) or a pharmaceutically-acceptable salt thereof, preserved with a cationic preservative. In one embodiment, the pharmaceutically-acceptable salt is sodium hyaluronate. In another embodiment, the cationic preservative includes benzalkonium chloride (BAK).

A first aspect of the invention provides a method for preparing a preserved hyaluronic acid composition, the method comprising: dissolving a cationic preservative in a first quantity of a solvent; dissolving a quantity of hyaluronic acid (HA) or physiologically-acceptable salt thereof in a second quantity of the solvent; and adding the dissolved HA or physiologically-acceptable salt thereof to the dissolved cationic preservative, wherein precipitation of the cationic preservative and the HA or physiologically-acceptable salt thereof is substantially prevented by dissolving each in the first and second quantities of solvent before they are combined.

A second aspect of the invention provides a method for preparing a preserved hyaluronic acid composition, the method comprising: dissolving a cationic preservative in a first quantity of a solvent; dissolving a quantity of hyaluronic acid (HA) or physiologically-acceptable salt thereof in a second quantity of the solvent; dissolving a quantity of an anionic cellulose derivative in a third quantity of the solvent; adding the dissolved HA or physiologically-acceptable salt thereof to the dissolved cationic preservative; and adding the dissolved anionic cellulose derivative to at least one of the following: the dissolved HA or physiologically-acceptable salt thereof, the dissolved cationic preservative, and the combined dissolved HA or physiologically-acceptable salt thereof and cationic preservative, wherein precipitation of the cationic preservative and the HA or physiologically-acceptable salt thereof is substantially prevented by dissolving each in the first and second quantities of solvent before they are combined.

A third aspect of the invention provides a preserved aqueous composition comprising: a solvent; hyaluronic acid (HA) or a physiologically-acceptable salt thereof; and an effective amount of a cationic preservative including benzalkonium chloride (BAK) having the formula $[C_6H_5CH_2N(CH_3)R]Cl$, wherein R is an alkyl group having at least one of: between eight and 10 and between 14 and 18 carbon atoms, wherein the composition is substantially free of precipitants of the cationic preservative and the HA or physiologically-acceptable salt thereof.

The illustrative aspects of the present invention are designed to solve the problems herein described and other problems not discussed, which are discoverable by a skilled artisan.

DETAILED DESCRIPTION

As indicated above, the invention provides a hyaluronic acid (HA) composition preserved with a cationic preservative such as benzalkonium chloride (BAK) and methods for its preparation.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

Where patents or patent applications are incorporated by reference herein and inconsistencies exist between the incorporated documents and the present disclosure, the present disclosure will prevail.

Surprisingly, it has been found that the conjugation and/or precipitation of HA and cationic preservatives such as BAK may be avoided or minimized by preparing separate HA and BAK solutions which are then combined.

More specifically, while the separate predilution of HA and BAK itself yields a combined composition exhibiting reduced HA-BAK conjugation and precipitation, the predilution of HA and BAK in particular ratios of solvent yields a combined composition exhibiting little or no HA-BAK conjugation and precipitation. In one embodiment, the HA or a pharmaceutically-acceptable salt thereof is dissolved in a quantity of solvent equal to about ⅓ the total desired volume of the final composition while the cationic preservative, such as BAK, is dissolved in a quantity of solvent equal to about ⅔ the total desired volume of the final composition. That is, the quantity of solvent used to dissolve the BAK is approximately twice that used to dissolve the HA.

For example, if one wished to prepare 300 mL of a preserved HA composition according to the invention, one could dissolve HA or a pharmaceutically-acceptable salt thereof (such as sodium hyaluronate) in about 100 mL of solvent and dissolve BAK and/or another cationic preservative in about 200 mL of solvent. Once the HA and BAK are dissolved in their respective quantities of solvent, the solutions are combined to yield a BAK-preserved composition exhibiting little or no HA-BAK conjugation or precipitation.

While the ratio of solvent quantities used to dissolve the BAK and HA is described above as about 2:1, this ratio is merely a preferred ratio. Effective compositions may be prepared with ratios between about 1.8:1 and 2.2:1.

Compositions according to the invention may be prepared using any number of solvents, subject to their suitability for administration. For ophthalmic, nasal, and otic compositions, the solvent is typically aqueous, comprising water alone or in combination with one or more other solvents. Suitable solvents for ophthalmic, nasal, and otic compositions include, for example, glycerin, polyethylene glycol (PEG), and propylene glycol.

Any species or combination of species of BAK may be used in practicing the invention. Generally defined, BAK has the formula: $[C_6H_5CH_2N(CH_3)R]Cl$, wherein R is an alkyl group having between eight and 18 carbon atoms.

Where BAK is the cationic preservative used, compositions according to the invention optionally contain between about 0.001% and about 0.02% BAK or, optionally, between about 0.002% and about 0.01% BAK, or, optionally, between about 0.003% and about 0.005% BAK, or, optionally about 0.005% BAK. Such concentrations of BAK may be obtained by diluting commercially-available BAK solutions, which are available in any number of concentrations. Most commercially-available BAK solutions contain between about 5% and about 50% BAK. In certain embodiments, the BAK solutions contain between about 10% and about 30% BAK, or, optionally, between about 15% and about 19% BAK, or, optionally, about 17% BAK. A more detailed discussion of BAK can be found in U.S. Patent Publication 20060069162, herein incorporated by reference in its entirety.

Similarly, any species or combination of species of HA may be used in practicing the invention. In certain embodiments, the HA has a molecular weight between about 500,000 daltons and about 4,000,000 daltons, or, optionally, between about 1,000,000 daltons and about 2,000,000 daltons, or, optionally, between about 1,200,000 daltons and about 1,800,000 daltons. Certain embodiments of the present invention contain between about 0.1% and about 0.5% HA, or, optionally, between about 0.2% and about 0.4% HA, or, optionally, about 0.2% HA. More detailed discussions of HA can be found in U.S. Patent Publication 20060094643; and U.S. Pat. Nos. 3,396,081; 3,862,003; 4,141,973; 4,517,296; 4,851,521; 4,965,353; 5,202,431; 5,316,926; 6,090,596; and 6,339,074, each of which patents are herein incorporated by reference in its entirety.

Once the HA and BAK solutions are combined, the composition may optionally be filtered to remove any minor HA-BAK precipitants or other agents affecting the composition's clarity. In certain embodiments, the compositions of the invention has a transmittance between about 93% and about 98% at 440 nm before filtration and a transmittance between about 95% and about 100% at 440 nm after filtration. Any method of filtration suitable for use with pharmaceutical compositions may be employed in practicing the invention.

Alternative cationic preservatives useful either alone or in combination with BAK include, but are not limited to, poly[dimethylimino-w-butene-1,4-diyl] chloride, alpha-[4-tris(2-hydroxyethyl)ammonium]-dichloride (Polyquaternium 1®), poly (oxyethyl (dimethyliminio)ethylene dmethyliminio) ethylene dichloride (WSCP®), benzalkonium halides other than BAK, salts of alexidine, alexidine-free base, salts of chlorhexidine, hexetidine, alkylamines, alkyl di- and tri-amine, Octenidine (N,N[prime]-(1,10-Decanediyldi-1-(4H)-pyridinyl-4-ylidenebis-[1-octanamine] dihydrochloride, cetylpyridinium chloride, cetylpyridinium salts, antimicrobial polypeptides, or mixtures thereof.

Compositions according to the invention may contain additional components, such as those commonly found in ophthalmic, nasal, and otic compositions. Such additional components include, for example, cellulose derivatives, medicaments (e.g., antibacterials, antifungals, etc.), and buffers (e.g., phosphate buffers, borate buffers, citrate buffers, etc.). Other components may be included in compositions according to the invention, depending upon how and where the composition is to be administered. A more detailed discussion of such components can be found in US Patent Publication 2007036829, herein incorporated by reference in its entirety.

A common class of additional components useful in ophthalmic, nasal, and otic compositions, is anionic cellulose derivatives. These may be defined as carboxyalkyl celluloses and hydroxyalkyl celluloses where the alkyl group includes between 1 and 3 carbon atoms. In certain embodiments, the anionic cellulose derivative is selected from the group consisting of, carboxymethylethylcellulose, ethyl carboxyethyl cellulose, carboxymethylhydroxyethylcelluloses, hydroxypropylmethylcelluloses, metal salts of carboxymethyl cellulose (such as sodium carboxymethyl cellulose) and mixtures thereof. In certain embodiments, the anionic cellulose derivative is a metal salt of carboxymethyl cellulose. Where used, one or more anionic cellulose derivatives may be dissolved in the fraction containing the cationic preservative, which is then combined with the fraction containing the HA or pharmaceutically-acceptable salt thereof. In certain embodiments, the anionic cellulose derivatives employed have molecular weight range of from about 70,000 daltons to about 700,000 daltons.

Alternatively, a third fraction of solvent may be separately employed to dissolve the CMC, which is then combined with the dissolved HA, the dissolved cationic preservative, or the combined HA (or pharmaceutically-acceptable salt) and cationic preservative fractions. In such an embodiment, the solvent fractions are optionally in a ratio of about 1:1:1. For example, if one were to prepare 300 mL of a composition according to the invention, about 100 mL of solvent would be used to separately dissolve the HA (or pharmaceutically-acceptable salt), the cationic preservative, and the CMC.

The preparation of compositions according to the invention will be described with reference to the following examples.

Example 1

Sodium Hyaluronate, BAK, CMC Composition Prepared in Two Parts

1. Dissolve a quantity of sodium hyaluronate in 100 mL of water to a concentration of 0.4%.
2. Dissolve a quantity of BAK in 200 mL of water to a concentration of 0.005%.
3. To the dissolved BAK, add and dissolve a quantity of CMC to a concentration of 0.5%.
4. Add the dissolved sodium hyaluronate solution to the dissolved BAK-CMC solution.

The method of Example 1 yielded 300 mL of an aqueous composition comprising: 0.133% sodium hyaluronate, 0.0033% BAK, and 0.33% CMC.

Example 2

Sodium Hyaluronate, BAK, CMC Composition Prepared in Three Parts

1. Dissolve a quantity of sodium hyaluronate in 100 mL of water to a concentration of 0.6%.
2. Dissolve a quantity of CMC in 100 mL of water to a concentration of 1.5%.
3. Dissolve a quantity of BAK in 100 mL of water to a concentration of 0.015%.
4. Add the dissolved sodium hyaluronate solution to the dissolved BAK solution.
5. Add the dissolved CMC solution to the combined sodium hyaluronate-BAK solution.
6. Filter the combined sodium hyaluronate-BAK-CMC solution.

The method of Example 2 yielded 300 mL of an aqueous composition comprising: 0.2% sodium hyaluronate, 0.005% BAK, and 0.5% CMC. The filtered solution had a transmittance of about 100%.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of the invention as defined by the accompanying claims.

What is claimed is:

1. A method for preparing a preserved hyaluronic acid composition, the method consisting essentially of:
   dissolving a cationic preservative which is poly[oxyethylene(dimethyliminio)ethylene(dimethyliminio)ethylenedichloride] in a first quantity of a solvent;
   dissolving a quantity of hyaluronic acid (HA) or physiologically-acceptable salt thereof in a second quantity of the solvent wherein the ratio of the first quantity of solvent to the second quantity of solvent is between 1.8:1 and 2.2:1; and
   adding the dissolved HA or physiologically-acceptable salt thereof to the dissolved cationic preservative,
   wherein precipitation of the cationic preservative and the HA or physiologically-acceptable salt thereof is substantially prevented by preparing separate HA or physiologically-acceptable salt thereof and separate cationic preservative solutions which are then combined.

2. The method of claim 1, wherein the physiologically-acceptable salt of HA includes sodium hyaluronate.

3. The method of claim 1, wherein the HA has a molecular weight between about 500,000 daltons and about 4,000,000 daltons.

4. The method of claim 3, wherein the molecular weight is between about 1,000,000 daltons and about 2,000,000 daltons.

5. The method of claim 1, wherein the solvent includes water.

6. The method of claim 5, wherein the solvent further consists essentially of at least one of the following: glycerin, polyethylene glycol (PEG), and propylene glycol.

7. The method of claim 1, wherein a ratio of the first quantity of the solvent to the second quantity of the solvent is between about 1.8:1 and about 2.2:1.

8. The method of claim 7, wherein the ratio is about 2:1.

9. The method of claim 1, further consisting essentially of:
   filtering the combined HA or physiologically-acceptable salt thereof and cationic preservative solution.

10. The method of claim 9, wherein the HA or physiologically-acceptable salt thereof and cationic preservative solution has a transmittance between about 93% and about 98% at 440 nm before filtration.

11. The method of claim 9, wherein the combined HA or physiologically-acceptable salt thereof and cationic preservative solution has a transmittance between about 95% and about 100% at 440 nm after filtration.

12. The method of claim 1, wherein the composition has a concentration of unprecipitated HA between about 0.1% and about 0.5%.

13. A composition prepared according to the method of claim 1.

14. A method for preparing a preserved hyaluronic acid composition, the method consisting essentially of:
   dissolving a cationic preservative which is poly[oxyethylene(dimethyliminio)ethylene(dimethyliminio)ethylenedichloride] in a first quantity of a solvent;
   dissolving a quantity of hyaluronic acid (HA) or physiologically-acceptable salt thereof in a second quantity of the solvent wherein the ratio of the first quantity of solvent to the second quantity of solvent is between 1.8:1 and 2.2:1;
   dissolving a quantity of an anionic cellulose derivative in a third quantity of the solvent;
   adding the dissolved HA or physiologically-acceptable salt thereof to the dissolved cationic preservative; and
   adding the dissolved anionic cellulose derivative to at least one of the following: the dissolved HA or physiologically-acceptable salt thereof, the dissolved cationic preservative, and the combined dissolved HA or physiologically-acceptable salt thereof and cationic preservative,
   wherein precipitation of the cationic preservative and the HA or physiologically-acceptable salt thereof is substantially prevented by preparing separate HA or physiologically-acceptable salt thereof and separate cationic preservative solutions which are then combined.

* * * * *